United States Patent
Miyazaki et al.

(10) Patent No.: US 7,846,231 B2
(45) Date of Patent: Dec. 7, 2010

(54) METHOD OF TREATING ORGANIC WASTE, AGENT FOR TREATING ORGANIC WASTE AND MICROORGANISMS TO BE USED THEREIN

(75) Inventors: Hiroshi Miyazaki, Tokyo (JP); Kiyoshi Maruta, Tokyo (JP); Tomohiro Hamaoka, Kanagawa (JP)

(73) Assignee: Calpis Co., Ltd., Tokyo (JP)

( * ) Notice: Subject to any disclaimer, the term of this patent is extended or adjusted under 35 U.S.C. 154(b) by 914 days.

(21) Appl. No.: 10/543,900

(22) PCT Filed: Jan. 29, 2004

(86) PCT No.: PCT/JP2004/000797

§ 371 (c)(1),
(2), (4) Date: Jul. 29, 2005

(87) PCT Pub. No.: WO2004/067197

PCT Pub. Date: Aug. 12, 2004

(65) Prior Publication Data

US 2006/0130545 A1 Jun. 22, 2006

(30) Foreign Application Priority Data

Jan. 31, 2003 (JP) .............................. 2003-024108

(51) Int. Cl.
| | |
|---|---|
| *C05F 11/08* | (2006.01) |
| *C05F 11/00* | (2006.01) |
| *C05F 3/00* | (2006.01) |
| *C05F 9/00* | (2006.01) |
| *C05F 1/00* | (2006.01) |
| *C05F 7/00* | (2006.01) |
| *C05D 9/02* | (2006.01) |
| *C12N 9/52* | (2006.01) |
| *C12N 9/54* | (2006.01) |
| *C12N 9/56* | (2006.01) |
| *A62D 3/30* | (2007.01) |

(52) U.S. Cl. .................... 71/6; 71/9; 71/11; 71/12; 71/13; 71/14; 71/15; 71/18; 71/21; 71/22; 71/25; 435/220; 435/221; 435/222; 588/313; 588/400; 588/405

(58) Field of Classification Search ............ 71/6, 71/9, 11, 12, 13, 14, 15, 18, 21, 22, 25
See application file for complete search history.

(56) References Cited

U.S. PATENT DOCUMENTS

| | | | | | |
|---|---|---|---|---|---|
| 6,074,451 | A | * | 6/2000 | Goda | 71/9 |
| 6,812,022 | B1 | * | 11/2004 | Aonuma | 435/252.5 |
| 2006/0130545 | A1 | * | 6/2006 | Miyazaki et al. | 71/6 |

FOREIGN PATENT DOCUMENTS

| | | |
|---|---|---|
| JP | 61-281091 | 12/1986 |
| JP | 6-157176 | 6/1994 |
| JP | 7-303478 | 11/1995 |
| JP | 9-12387 | 1/1997 |
| JP | 2001-103962 | 4/2001 |
| JP | 2001-187375 | 7/2001 |
| JP | 2001187375 A * | 7/2001 |
| JP | 2002-58471 | 2/2002 |

OTHER PUBLICATIONS

Blanc et al. "Rapid Identification . . . " International Journal of Systematic Bacteriology, Oct. 1997, 1246-1248.*
Fang et al. "Digestion Activity . . . " Water, Air and Soil Pollution 126: 1-12, 2001.*
Michel Blanc, et al., "Rapid Identification of Heterotrophic, Thermophilic, Spore Forming Bacteria Isolated from Hot composts", International Journal of Systematic Bacteriology, vol. 47, No. 4, XP-002424367, Oct. 1997, pp. 1246-1248.

* cited by examiner

*Primary Examiner*—Jerry Lorengo
*Assistant Examiner*—Jennifer A Smith
(74) *Attorney, Agent, or Firm*—Oblon, Spivak, McClelland, Maier & Neustadt, L.L.P.

(57) ABSTRACT

There are provided a method of treating organic waste, which is excellent in the smooth temperature elevation in the early stage of the treatment and satisfactory in temperature-maintenance in a high temperature range, and by which the stable treatment of organic waste is achieved and the evaporation of moisture is promoted, thereby a stable effect of treating organic waste and an increased treatment scale being achieved; an agent for treating organic waste; and microorganisms to be used therein. The method is characterized by the use of a mesophilic bacterium showing its activity at 15 to 50° C. and a thermophilic bacterium showing its activity at 50 to 70° C. in the organic waste. As the mesophilic bacteria, bacteria which have an exothermic action and form spores under a temperature of 50° C. or higher are preferable and *Bacillus subtilis* is more preferable. Among these bacteria, a C-3102 strain (FERM BP-1096) is especially preferable. As the thermophilic bacteria, *Bacillus pallidus* is preferable and, among these bacteria, a TK6004 strain (FERM BP-08597) is more preferable.

23 Claims, 3 Drawing Sheets

METHOD OF TREATING ORGANIC WASTE, AGENT FOR TREATING ORGANIC WASTE AND MICROORGANISMS TO BE USED THEREIN

TECHNICAL FIELD

The present invention relates to a method of treating an organic waste using useful microorganisms, an agent for treating an organic waste, and the useful microorganisms to be used therein.

BACKGROUND ART

Recently, raw garbage discharged from household and business in urban area, feces and urine in the livestock field including cow dung and poultry manure, organic waste derived from swage treatment, organic industrial waste, and the like have remarkably increased, and hence the facilities for treating them are at the absolute edge of exceeding their capacity.

In such a situation, it has been proposed to convert those wastes into compost through decomposition/digestion treatment or composting thereof by the action of microorganisms. However, the microorganisms involved in decomposition/digestion thereof are usually derived from self-generation, and hence it requires a long period of time to achieve a certain concentration of the microorganisms necessary for the treatment.

On the other hand, in a continuously-working system such as a raw garbage-treating machine, according to the frequently-repeated rise and fall of material temperature, bacterial flora is not stabilized, and it becomes one of the factors of affording no stable effect. As a means for accelerating microorganism generation and promoting efficient treatment, treating agents containing various microorganisms and the like have been also disclosed.

For example, with focusing on the process in which the material temperature of organic waste is elevated from the room temperature to a high temperature of about 50 to 70° C., a treating agent in which spores of the genus *Bacillus* are mixed has been disclosed as a treating agent for composting organic waste, for the purpose of maintaining the temperature in the process (for example, cf. Patent Document 1).

However, in a high temperature range, since these microorganisms stop their action to form cysts, a large rise and fall of the material temperature during the treatment is observed, and hence bacterial flora is destabilized. Accordingly, it invites a lowered pH of the object to be treated and a proliferation of unwanted bacteria to cause a decrease in treating efficiency, malodor, and the like. Thus, there arises a problem that the stable treating effect cannot be obtained. Furthermore, since moisture is not evaporated at a high temperature, it is necessary to control an initial water content, and hence there is a problem in view of labor and cost.

Additionally, there has been disclosed a method in which a rapid temperature elevation and a high protease activity at 50° C. or higher are achieved using a microorganism belonging to bacteria of *Bacillus* to improve the decomposition-treating capacity of organic waste (for example, cf. Patent Document 2).

However, it is necessary to culture the bacteria for use in the treatment for 3 days beforehand, and hence the method is far from the substantial improvement. Furthermore, since it is necessary to use the bacteria in the same amount as that of the object to be treated in the actual treatment, there is a problem in view of a treating capacity and cost.

Patent Document 1: JP-A-9-12387 (pages 1 to 2)

Patent Document 2: JP-A-7-303478 (pages 1 to 2)

An object of the present invention is to overcome the defects of the above conventional technologies, and the present invention provides a method of treating organic waste, which is excellent in smooth temperature elevation in the early stage of the treatment and is satisfactory in temperature-maintenance in a high temperature range, and by which a stable treatment of organic waste can be achieved and the evaporation of moisture is promoted, thereby a stable effect of treating organic waste and an increase in treatment scale being achieved; an agent for treating organic waste; and microorganisms to be used therein.

DISCLOSURE OF THE INVENTION

As a result of the extensive studies for solving the above problems, the present inventors found that the above problems can be solved by combining certain types of bacteria and allowing them to exist in organic waste.

Namely, the invention is as follows.

(1) A method of treating organic waste, which comprises allowing a mesophilic bacterium which exerts its activity at 15 to 50° C. and a thermophilic bacterium which exerts its activity at 50 to 70° C. to be present in the organic waste.

(2) The method of treating organic waste according to (1) above, which further comprises adding the mesophilic bacterium and the thermophilic bacterium to the organic waste.

(3) The method of treating organic waste according to (1) or (2) above, which further comprises adding new organic waste to the organic waste in which the mesophilic bacterium and the thermophilic bacterium are present.

(4) The method of treating organic waste according to any one of (1) to (3) above, wherein the mesophilic bacterium or the thermophilic bacterium has a decomposition ability of organic matter.

(5) The method of treating organic waste according to any one of (1) to (4) above, wherein the mesophilic bacterium has an exothermic action.

(6) The method of treating organic waste according to any one of (1) to (5) above, wherein the mesophilic bacterium forms a spore at a temperature of 50° C. or higher.

(7) The method of treating organic waste according to any one of (1) to (6) above, wherein the mesophilic bacterium belongs to the genus *Bacillus*.

(8) The method of treating organic waste according to (7), wherein the mesophilic bacterium is *Bacillus subtilis*.

(9) The method of treating organic waste according to (8) above, wherein the mesophilic bacterium is a strain of *Bacillus subtilis* C-3102 (FERM BP-1096).

(10) The method of treating organic waste according to any one of (1) to (4) above, wherein the thermophilic bacterium belongs to the genus *Bacillus*.

(11) The method of treating organic waste according to (10) above, wherein the thermophilic bacterium is *Bacillus pallidus*.

(12) The method of treating organic waste according to (11) above, wherein the thermophilic bacterium is a strain of *Bacillus pallidus* TK6004 (FERM BP-08597).

(13) The method of treating organic waste according to any one of (1) to (12) above, wherein the mesophilic bacterium in said waste is present at a cell mass of from $1.0 \times 10^3$ to $1.0 \times 10^8$ CFU/g.

(14) The method of treating organic waste according to any one of (1) to (13) above, wherein the thermophilic bacterium in said waste is present at a cell mass of from $1.0 \times 10^3$ to $1.0 \times 10^8$ CFU/g.

(15) The method of treating organic waste according to any one of (1) to (14) above, wherein the organic waste is raw garbage, livestock waste, waste derived from sewage treatment, or industrial waste.

(16) An agent for treating organic waste, which contains a mesophilic bacterium which exerts its activity at 15 to 50° C. and a thermophilic bacterium which exerts its activity at 50 to 70° C.

(17) The agent for treating organic waste according to (16) above, wherein the mesophilic bacterium or the thermophilic bacterium has a decomposition ability of organic matter.

(18) The agent for treating organic waste according to (16) or (17) above, wherein the mesophilic bacterium has an exothermic action.

(19) The agent for treating organic waste according to any one of (16) to (18) above, wherein the mesophilic bacterium forms a spore at a temperature of 50° C. or higher.

(20) The agent for treating organic waste according to any one of (16) to (19) above, wherein the mesophilic bacterium belongs to the genus *Bacillus*.

(21) The agent for treating organic waste according to (20) above, wherein the mesophilic bacterium is *Bacillus subtilis*.

(22) The agent for treating organic waste according to (21) above, wherein the mesophilic bacterium is a strain of *Bacillus subtilis* C-3102 (FERM BP-1096).

(23) The agent for treating organic waste according to (16) or (17) above, wherein the thermophilic bacterium belongs to the genus *Bacillus*.

(24) The agent for treating organic waste according to (23) above, wherein the thermophilic bacterium is *Bacillus pallidus*.

(25) The agent for treating organic waste according to (24) above, wherein the thermophilic bacterium is a strain of *Bacillus pallidus* TK6004 (FERM BP-08597).

(26) *Bacillus pallidus* which exerts its activity at 50 to 70° C.

(27) The *Bacillus pallidus* according to (26) above, which has a decomposition ability of organic matter.

(28) A strain of *Bacillus pallidus* TK6004 (FERM BP-08597).

With regard to the mesophilic bacterium and the thermophilic bacterium for use in the present invention, the term "exerting its activity" means that not only a bacterium is alive within the temperature range in which the bacterium can alive but also the bacterium itself can grow through decomposition or assimilation of organic matter.

In the early stage of the microbial decomposition according to the present invention, the material temperature of the object to be treated can be rapidly elevated to a high temperature by the spontaneous heat-generation induced by the mesophilic bacterium exerting its activity in a moderate temperature range. After the temperature reaches optimum temperature of the thermophilic bacterium, maintenance of the material temperature and decomposition of the object to be treated can be efficiently conducted by the spontaneous heat-generation induced by the thermophilic bacterium exerting its activity in a high temperature range. Thereby, in a stable high-temperature state, the evaporation of the moisture contained in the object to be treated is further accelerated, and the amount of the object to be treated can be decreased.

On the other hand, when a bacterium which exists as a pore and is in a dormant state in a high temperature range is used as a mesophilic bacterium, in the case that the material temperature of the object to be treated is lowered by some causes such as a charge of new waste and stirring, the methophilic bacterium germinates again and starts its activity to elevate the material temperature. Thereby, the material temperature of the object to be treated is stabilized and the high temperature is maintained.

In comparison with the conventional methods, the maintenance of the material temperature of the object to be treated at a high temperature is enabled. In addition, by combining the bacteria having the most suitable activity according to each temperature, effective digestive decomposition is promoted, and the treatment scale is increased.

BEST MODE FOR CARRYING OUT THE INVENTION

Figure 1:
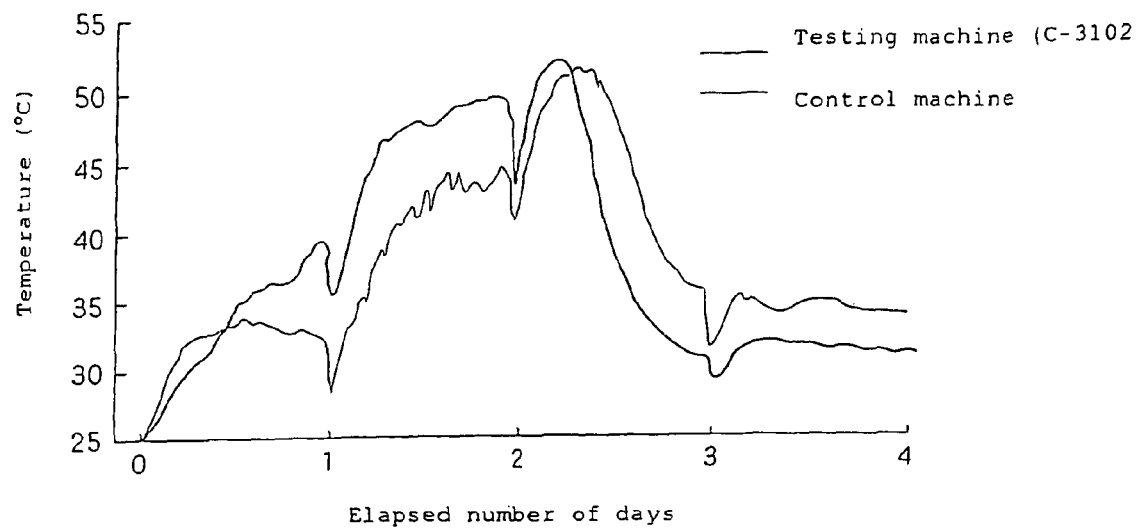
FIG. 1 is a graph in which changes of the temperature in a testing machine using *Bacillus subtilis* C-3102 strain and in the control machine in Example 1 are compared.

The mesophilic bacterium used in the present invention is not particularly limited as far as it exerts its activity at 15 to 50° C., but it preferably has an exothermic action to elevate material temperature from a low temperature to a high temperature range. Moreover, it preferably forms a spore in a high temperature range of 50° C. or higher.

The spore formation is a property of forming spores resistant to the conditions inconvenient for the growth, such as deficiency of nutrition, dryness, or heat, to thereby achieve self-conservation, when the bacterium is under these conditions.

The thermophilic bacterium used in the present invention is not particularly limited as far as it exerts its activity at 50 to 70° C.

Moreover, at least one of these mesophilic bacterium and thermophilic bacterium preferably has a decomposition ability of organic matter.

The decomposition ability of organic matter is a property possessed by microorganisms decomposing and digesting organic waste such as carbohydrates, proteins and lipids. Further, the exothermic action means an exothermic action induced by the decomposition of organic waste due to the microorganisms or enzymes formed from the microorganisms, in the process of the decomposition/digestion.

Furthermore, the location of these mesophilic bacterium and thermophilic bacterium in the biological classification is not particularly limited, but the genus *Bacillus* or the like may be mentioned.

As the mesophilic bacterium and the thermophilic bacterium in the present invention, more specifically, there may be mentioned, as bacterial species belonging to the genus *Bacil-*

*lus, Bacillus subtilis, Bacillus anthracis, Bacillus azotoformans, Bacillus brevis, Bacillus cereus, Bacillus circulans, Bacillus coagulans, Bacillus lentus, Bacillus lichemformis, Bacillus megaterium, Bacillus natto, Bacillus steanothermophilus, Bacillus pallidus*, and the like. As the mesophilic bacterium, *Bacillus subtilis* is preferable, and as the thermophilic bacterium, *Bacillus pallidus* is preferable.

A preferable example of the mesophilic bacterium of the present invention is a strain of *Bacillus subtilis* C-3102.

The *Bacillus subtilis* C-3102 strain, a known strain, was originally deposited in International Patent Organism Depository, National Institute of Advanced Industrial Science and Technology (at the time of deposit; Fermentation Research Institute, Agency of Industrial Science and Technology, Department of Trade and Industry, Japan) of 1-1, Higashi 1-chome, Tsukuba-shi, Ibaraki, Japan (at the time of deposit; 1-3, Higashi 1-chome, Yatabe-cho, Tsukuba-gun, Ibaraki, Japan), under FERM P-8584 on Dec. 25, 1985, which was then transferred to international deposition in the same organization under FERM BP-1096 (at the time of transfer; under FERM BP-1096) on Jun. 28, 1986. In this connection, the bacteriological properties of *Bacillus subtilis* C-3102 (FERM BP-1096) is described in JP-A-63-209580 and JP-A-62-232343 which have been already opened to public.

For culturing the above *Bacillus subtilis* C-3102 (FERM BP-1096), for example, a liquid medium or a solid medium containing a carbon source, a nitrogen source, inorganic substances, and the like, which is usually employed for culturing microorganisms can be used as a culture medium. The carbon source may be an assimilable carbon source, and examples thereof include glucose, sucrose, starch, molasses, and the like. Examples of the nitrogen source include peptone, meat extract, casein acid hydrolysate, ammonium sulfate, and the like. In addition, there may be optionally added salts such as phosphate salts, magnesium, sodium, potassium, calcium, iron, and manganese; vitamins; amino acids; an antifoaming agent; a surfactant; and the like. Moreover, the culture may be preferably performed under an aerobic condition, and it is preferable that the initial pH of the medium is from 5 to 9, particularly from 6 to 8, the culture temperature is from 20 to 50° C., particularly from 35 to 40° C., and the culture time is from 12 hours to 7 days.

A preferable example of the thermophilic bacterium of the present invention is a strain of *Bacillus pallidus* TK6004 as a new strain. The *Bacillus pallidus* TK6004 strain was originally deposited in International Patent Organism Depository, National Institute of Advanced Industrial Science and Technology in 1-1, Higashi 1-chome, Tsukuba-shi, Ibaraki, Japan, under FERM P-18983 on Aug. 22, 2002, which was then transferred to international deposition in the same organization under FERM BP-08597 on Jan. 20, 2004.

The *Bacillus pallidus* TK6004 strain was separated from leaf mold.

The separation method and the bacteriological properties of this strain are described below.

Separation Method of a Thermophilic Bacterium, a Strain of *Bacillus pallidus* TK6004 (FERM BP-08597)

(1) Leaf mold made of fallen leaves at a practical farmer in Sagamihara-shi of Kanagawa prefecture was added to (sterile) raw garbage to confirm the temperature elevation (50° C. or higher). Thermophilic bacteria at the time of the temperature elevation were separated.

Specifically, the raw garbage sample at the time of the temperature elevation was pulverized under ice cooling, and an appropriate amount thereof was diluted with physiological saline. The diluted sample was stirred under ice cooling for 20 minutes to suspend the microorganisms. Subsequently, they were cultured on a TS medium and then particularly predominant four strains were collected.

(2) The collected four strains were isolated and cultured to confirm the temperature-elevating ability. Each of the four strains was put into (sterile) raw garbage in a single strain state to confirm the elevation of the temperature. As a result, the temperature elevation of the raw garbage was confirmed on two strains, TK6003 and TK6004.

(3) Simple test for confirming production aptitude of two strains, TK6003 and TK6004

Conditions for spore formation: After being exposed to a drying condition at 70° C., the strains were investigated under microscopic inspection. As a result, a tendency to spore formation was observed on TK6004 but the tendency was not observed on TK6003.

Through the above separation method and production aptitude test, the TK6004 strain was separated and selected as the thermophilic bacterium of the present invention.

In this connection, the screening condition at the separation of the above TK6004 strain was defined as whether the elevation of temperature from room temperature to 50° C. or higher and the presence of activity at 50° C. or higher were confirmed.

However, a bacterium exerting its strong activity at 50° C. or higher but no activity at 50° C. or lower is also applicable as the thermophilic bacterium of the present invention.

Therefore, in order to separate the microorganism applicable as the thermophilic bacterium of the present invention, it can be separated by not only the above method but also a method of confirming the elevation of temperature to a higher temperature range and the presence of activity at 50° C. or higher, due to the addition of the bacterium to (sterile) raw garbage elevated to about 50° C. beforehand according to the other means.

Bacteriological Properties of Thermophilic Bacterium *Bacillus pallidus* TK6004 Strain (a) Morphological properties (1) Shape of cells: rod
  Size of cells: 0.7 to 0.8×1.5 to 2.0 μm (2) Polymorphism: −

(3) Mobility: +

(4) Spore formation: +

(b) Cultural properties
  TS (Trypticase Soy; Becton Dickinson, N.J., U.S.A.) agar medium: round, wavy rim, low and flat, non-glossy, cream (c) Physiological Properties (1) Gram stainability: indefinite (2) Reduction of nitrate: −

(3) MR test: +

(4) VP test: −

(5) Production of indole: −

(6) Production of hydrogen sulfide: −

(7) Utilization of citrate: −

(8) Urease: −

(9) Oxidase: +

(10) Catalase: +

(11) Growth temperature range: 30 to about 70° C.

(12) Attitude to oxygen (discrimination between aerobic and anaerobic, etc.): aerobic

(13) Production of acid

| | | |
|---|---|---|
| 1) | D-arabinose | − |
| 2) | L-arabinose | + |
| 3) | D-xylose | − |
| 4) | L-xylose | − |
| 5) | D-glucose | + |
| 6) | D-mannose | + |
| 7) | D-fructose | + |
| 8) | D-galactose | − |
| 9) | maltose | + |
| 10) | sucrose | − |
| 11) | lactose | − |
| 12) | trehalose | + |
| 13) | D-sorbitol | + |
| 14) | D-mannitol | + |
| 15) | inositol | − |
| 16) | starch | + |

(14) Casein decomposition: −

(15) Sodium chloride resistance (10%): −

(d) Chemical taxonomic properties

DNA-DNA Homology with Closely-Related Species

Homology of 16S rDNA with closely-related species was analyzed.

For the DNA information on the closely-related species to be compared at the homology analysis, a database MicroSeq Bacterial Full Gene Library v.0001 (Applied Biosystems, U.S.A.) was employed. Homology of *Bacillus pallidus* TK6004 strain with high-ranking 10 strains of the closely-related species is shown below.

*Bacillus pallidus*: 99.87%
*Bacillus smithii*: 91.03%
*Bacillus thermoglucosidasius*: 90.38%
*Bacillus kaustophilus*: 90.25%
*Bacillus thermoleovorans*: 90.25%
*Bacillus thermocatenulatus*: 89.93%
*Bacillus lentus*: 89.92%
*Bacillus licheniformis*: 89.90%
*Bacillus stearothermophilus*: 89.86%
*Bacillus coagulans*: 89.41%

In order to culture the above *Bacillus pallidus* TK6004 strain (FERM BP-08597), for example, the culture media same as those used for culturing *Bacillus subtilis* C-3102 (FERM BP-1096) can be used as the media. Moreover, as culture conditions, the culture is preferably performed under aerobic conditions, and it is preferable that the initial pH of the medium is from 5 to 9, particularly from 6 to 8, the culture temperature is from 30 to 60° C., particularly from 50 to 60° C., and the culture time is from 12 hours to 7 days.

The cell mass of the mesophilic bacterium in the organic waste according to the method of treating organic waste in the present invention is not particularly limited, but is preferably in the range of from $1.0 \times 10^3$ to $1.0 \times 10^8$ CFU/g, more preferably in the range of from $1.0 \times 10^5$ to $1.0 \times 10^8$ CFU/g.

Moreover, the cell mass of the thermophilic bacterium in the organic waste is not particularly limited but is preferably in the range of from $1.0 \times 10^3$ to $1.0 \times 10^8$ CFU/g, more preferably in the range of from $1.0 \times 10^3$ to $1.0 \times 10^6$ CFU/g.

At the application of the mesophilic bacterium and the thermophilic bacterium to the method of treating organic waste according to the present invention, the method of adding and charging of the bacterial bodies and organic waste is not particularly limited. The bacterial bodies of the mesophilic bacterium and thermophilic bacterium may be added and charged to organic waste at once, or may be added and charged with dividing them at a plurality of stages. Further, the respective mesophilic bacterium and thermophilic bacterium may be separately added and charged. In this connection, from the advantageous viewpoint of operational efficiency according to the present invention, it is preferable to use the method of adding and charging the bacterial bodies of the mesophilic bacterium and thermophilic bacterium to organic waste at once.

In the method of treating organic waste according to the present invention, as the method of adding and charging organic waste, the organic waste may be previously added and charged to a container for treatment or the like all at once, or the organic waste may be added and charged with dividing the organic waste at a plurality of stages so that a new portion is added and charged after the organic waste previously charged is decomposed and its volume is reduced to some extent.

Moreover, in the method of treating organic waste according to the present invention, the form of the mesophilic bacterium and thermophilic bacterium for use in the addition and charging is not particularly limited, but the culture liquid of viable bacteria cultured in a liquid medium may be used without further treatment or concentrated viable bacterial bodies obtained by collecting viable bacteria cultured in a liquid medium by centrifugation may be also used. In addition, freeze-dried bacterial bodies may be also suitable. Moreover, when the mesophilic bacterium and thermophilic bacterium form spores, the spores may be employed.

In this connection, in the method of treating organic waste according to the present invention, the organic waste is not particularly limited, but there may be mentioned raw garbage, livestock waste, waste derived from sewage treatment, or industrial waste.

The raw garbage is organic waste discharged from household and business, which can be decomposed by the action of microorganisms.

The livestock waste means organic waste such as feces and urine of livestock and poultry, including cow dung and poultry manure, which is discharged from livestock farming and processing of livestock.

The waste derived from sewage treatment means surplus sludge and the like, by-produced and discharged by activated sludge process and the like.

The industrial waste includes the above raw garbage discharged from business, livestock waste, waste derived from sewage treatment, and the like.

The form of the above mesophilic bacterium and thermophilic bacterium at the application to the agent for treating organic waste according to the present invention is not particularly limited like the form of addition and discharge of the mesophilic bacterium and thermophilic bacterium for use in the above treating method, but the culture liquid of viable bacteria cultured in a liquid medium may be used. Moreover, concentrated viable bacterial bodies obtained by collecting viable bacteria cultured in a liquid medium by centrifugation or the like, or freeze-dried bacterial bodies may be used. In addition, when the mesophilic bacterium and thermophilic bacterium form spores, the spores may be employed.

The following will specifically describe the present invention based on Examples, but the invention is not limited thereto.

EXAMPLE 1

Exothermic Action by Mesophilic Bacterium *Bacillus subtilis* C-3102

Tests were carried out using two household garbage-treating machines (SANYO: SNS-M15). The machine has a raw garbage-treating capacity of 700 g per day (recommended amount by the manufacturer). Thereto was charged 4.5 kg (recommended amount by the manufacturer) of whole chip (SNM-HK13) designated by the manufacturer, and then the experiment was started. Further, a thermometer (Thermo Recorder TR-51: T & D Corporation) was set at the stirring rod of the garbage-treating machine to measure and record the inner temperature every 5 minutes.

In the experiment, food residue discharged from the canteen in Sagami Plant of Calpis Co., Ltd. was used. The raw garbage was used in the experiment after putting the raw garbage into a homogeneous state by stirring and mixing the whole amount thereof.

One of the garbage-treating machines was used as a testing machine and 30 g ($1 \times 10^{10}$ CFU/g) of bacterial powder of *Bacillus subtilis* C-3102 was added thereto at the start of the experiment by charging the raw garbage. Another machine was used as a control machine and was operated according to the manufacturer's instruction. Into both of the testing machine and control machine, 1.5 kg of the raw garbage, which corresponded to an amount about twice the amount recommended by the manufacturer, was charged at 14 o'clock every day. At the discharge of the raw garbage, total weight of the machine was measured and a digested amount per one day was determined based on the difference from the weight on the preceding day.

In this connection, the bacterial powder was obtained by thermally drying viable bacterial bodies after culture to thereby induce spore formation and, after complete evaporation of moisture, pulverizing them to form a powder.

The results are shown below.

As shown in FIG. 1, the inner temperature of the testing machine to which *Bacillus subtilis* C-3102 was charged reached 50° C. on second day, and the temperature elevated rapidly in comparison with the control machine. Since the mesophilic bacterium *Bacillus subtilis* C-3102 cannot grow at a high temperature of 50° C. or higher, the temperature rapidly lowered after it reached growth-limiting temperature. The temperature elevation in the control machine is attributable to the conventional bacteria, and the temperature reached 50° C. after a delay of one day in comparison with the testing machine.

Figure 2:
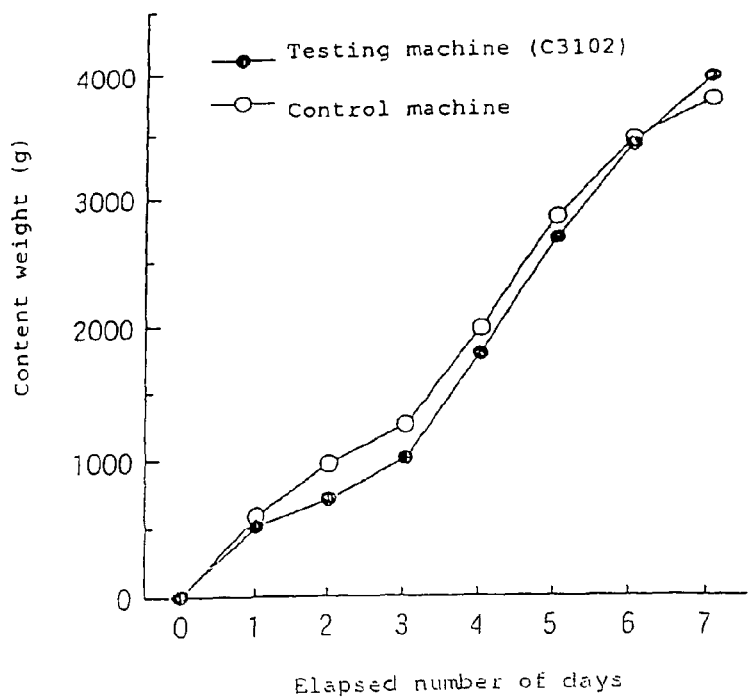
FIG. 2 is a graph in which changes of the content weight in a testing machine using *Bacillus subtilis* C-3102 strain and in the control machine in Example 1 are compared.

The change of content weight of the garbage-treating machine is shown in FIG. 2. The axis of ordinate shows content weight (g) and the axis of abscissas shows the elapsed number of days from the start of the test. As a result of charging raw garbage twice as much as the amount recommended by manufacturer, undigested raw garbage continued to be accumulated in the inside and the inner weight kept on increasing in both of the control machine and the testing machine. For two days immediately after the start of the experiment, since the temperature was elevated in the testing machine faster than in the control machine, the decomposition of the raw garbage was promoted, and hence a tendency that the increase in the inner weight was slightly slow in comparison with the control plot was observed.

EXAMPLE 2

Decomposition Action Induced by Thermophilic Bacterium *Bacillus pallidus* TK6004

For clarifying the action of the thermophilic bacterium *Bacillus pallidus* TK6004, tests were carried out using the household garbage-treating machines (SANYO: SNS-M15) as in Example 1. In the experiments, as in Example 1, into the testing machine and control machine, 1.5 kg of the raw garbage was charged at 14 o'clock every day. Into a testing machine, 30 g ($1 \times 10^6$ CFU/g) of bacterial powder of the thermophilic bacterium *Bacillus pallidus* TK6004 was added thereto at the start of the experiment by charging the raw garbage. Moreover, by the same means as in Example 1, the temperature and treated amount were measured and compared with those in the control machine.

The results are shown below.

Figure 3:
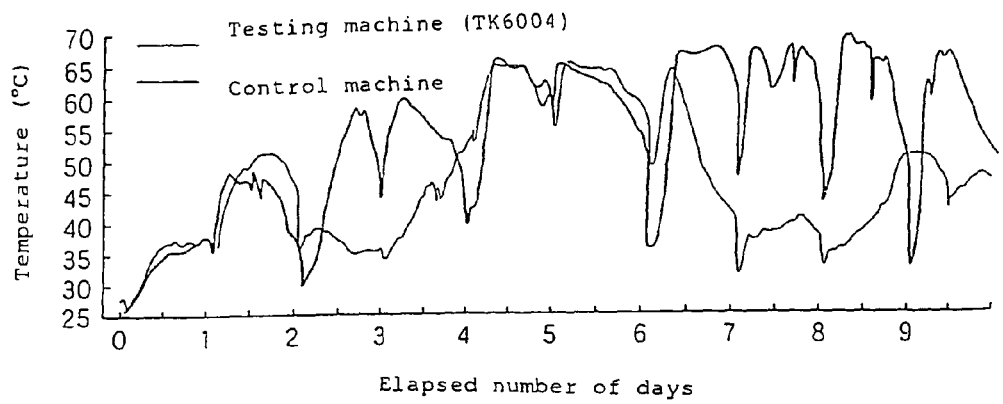
FIG. 3 is a graph in which changes of the temperature in a testing machine using *Bacillus pallidus* TK6004 strain and in the control machine in Example 2 are compared.

As shown in FIG. 3, the inner temperature of the testing machine reached 65° C. on fourth day and the high temperature was maintained after that time. However, since the initial temperature elevation was derived from the conventional bacteria, a result that the initial temperature elevation was slow was observed. On the other hand, the inner temperature of the control machine was not stabilized. Thus, it is understood that the thermophilic bacterium *Bacillus pallidus* TK6004 is effective for the elevation of the inner temperature to a high temperature and the maintenance thereof.

Figure 4:
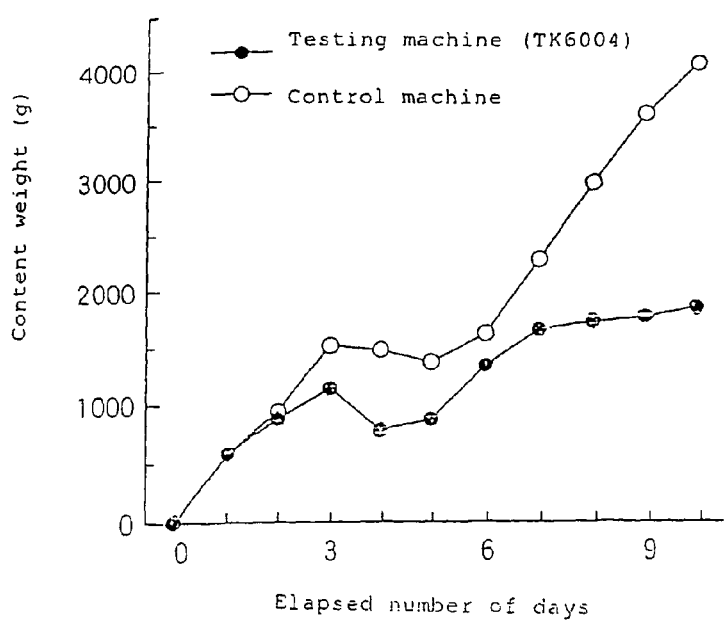
FIG. 4 is a graph in which changes of the content weight in a testing machine using *Bacillus pallidus* TK6004 strain and in the control machine in Example 2 are compared.

FIG. 4 shows the change of content weight of the garbage-treating machine. The treating machine continued to treat 1400 g of raw garbage which was nearly twice as much as the amount recommended by the manufacturer after fourth day at which the inner temperature reached 65° C. On the other hand, in the control machine, undigested raw garbage was accumulated in the inside, and a tendency that the content weight increased was observed. By charging the thermophilic bacterium *Bacillus pallidus* TK6004, it became possible to treat raw garbage nearly twice as much as the amount recommended by the manufacturer.

EXAMPLE 3

Combination of Mesophilic Bacterium, *Bacillus subtilis* C-3102 and Thermophilic Bacterium, *Bacillus pallidus* TK6004

By utilizing the mesophilic bacterium *Bacillus subtilis* C-3102, the initial temperature elevation is ensured without any mechanical means. However, since the high temperature is not maintained, it is not possible to promote an efficient stable treatment. By providing the thermophilic bacterium *Bacillus pallidus* TK6004, it is possible to maintain the inside of the machine at a high temperature to promote highly efficient treatment. However, the temperature elevation to the temperature range in which the thermophilic bacterium *Bacillus pallidus* TK6004 can act has to rely on the machines or the action of conventional bacteria. The temperature elevation by a machine is reliable, but the economical burden is large. The action of the conventional bacteria requires time, and also, it is not stable. Therefore, if it is possible to elevate the temperature by the mesophilic bacterium and maintain the high temperature by the thermophilic bacterium *Bacillus pallidus*, the method may be an inexpensive means capable of avoiding these defects.

Two machines of a garbage-treating machine (SANYO: SNS-M15) were employed and a comparative experiment was performed. One machine was used as a control machine, and another was used as a testing machine. At the start of the experiment, 30 g ($1\times10^8$ CFU/g) of bacterial powder of the mesophilic bacterium *Bacillus subtilis* C-3102 was charged thereto. Moreover, 40 g ($1\times10^8$ CFU/g) of bacterial powder of the thermophilic bacterium *Bacillus pallidus* TK6004 was charged every time when the raw garbage was charged. In the experiment, food residue discharged from the canteen in Sagami Plant of Calpis Co., Ltd. was used and 1.5 kg of raw garbage, which was twice as much as the amount recommended by the manufacturer, was charged at 14 o'clock every day. During the test period, the temperature and the weight were measured to be used as the measure of the decomposed amount.

Figure 5:
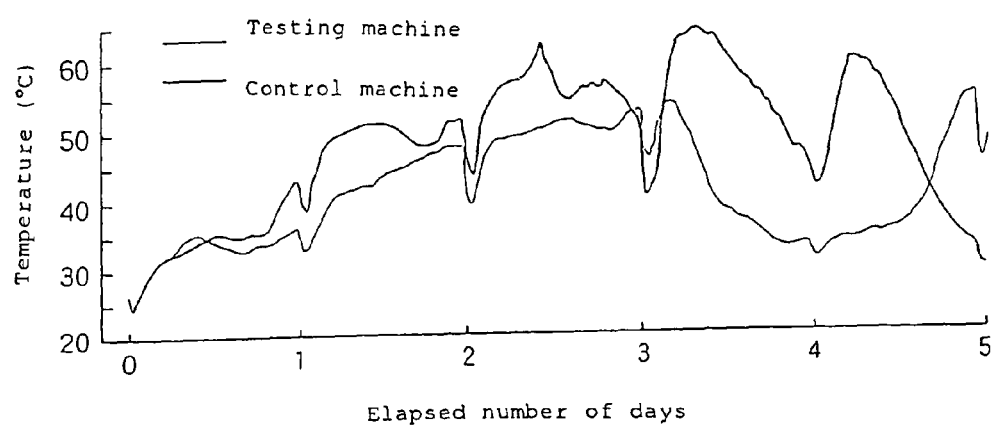
FIG. 5 is a graph in which changes of the temperature in a testing machine using *Bacillus subtilis* C-3102 strain and *Bacillus pallidus* TK6004 strain and in the control machine in Example 3 are compared.

As shown in FIG. 5, in the testing machine, after the temperature elevation by the action of the mesophilic bacterium *Bacillus subtilis* C-3102, there was observed that the thermophilic bacterium *Bacillus pallidus* TK6004 elevated the inner temperature to 60° C. or higher. On the other hand, in the control machine, although the inner temperature gradually increased by the action of conventional bacteria, the temperature did not elevate to 53° C. or higher.

Figure 6:
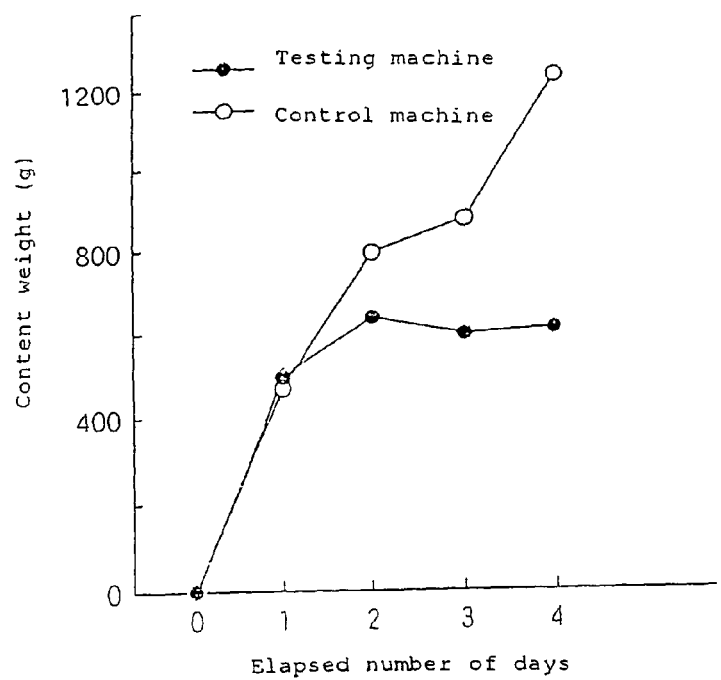
FIG. 6 is a graph in which changes of the content weight in a testing machine using *Bacillus subtilis* C-3102 strain and *Bacillus pallidus* TK6004 strain and in the control machine in Example 3 are compared.

The change of content weight of the garbage-treating machine is shown in FIG. 6.

Since the temperature rapidly elevated and maintained in the testing machine, the machine maintained the treated amount of the raw garbage of 1500 g/day which was nearly twice as much as the amount recommended by the manufacturer, and the content weight did not increase. In the control machine, 1500 g of the raw garbage was not thoroughly digested, and the content weight gradually increased. As described above, by elevating the inner temperature of the treating machine by the action of the mesophilic bacterium *Bacillus subtilis* C-3102 and further elevating and maintaining the temperature by the action of the thermophilic bacterium, *Bacillus pallidus* TK6004, it is possible to make the treatment with a commercially available garbage-treating machine more efficient.

INDUSTRIAL APPLICABILITY

By using a combination of a mesophilic bacterium and a thermophilic bacterium as microorganisms involved in the decomposition/digestion of the organic waste according to the present invention, smooth temperature elevation through spontaneous heat generation by the action of the mesophilic bacterium is achieved, and further, decomposition/digestion within a high temperature range is continuously preformed at an optimum temperature of the thermophilic bacterium, so that a high efficiency of the decomposition treatment can be accomplished, in comparison with the method which relies on self-generated microorganisms or microorganisms derived from treated organic waste.

Moreover, by using microorganisms for treatment composed of combined mesophilic bacterium and thermophilic bacterium, a microorganism flora is always constant and, as a result, it is possible to eliminate causes inducing proliferation of unwanted bacteria, a lowering of pH of the objects to be treated, a decrease in treating efficiency, malodor, and the like.

Furthermore, by adding the mesophilic bacterium, heating to a high temperature range in which the thermophilic bacterium starts to act by an external apparatus is not necessary, and thus the method is excellent in view of energy saving.

The invention claimed is:

1. A method of treating organic waste, comprising:
   providing two different bacteria, wherein a first bacterium is a mesophilic bacterium which exerts its activity at 15 to 50° C. and a second bacterium is a thermophilic bacterium which exerts its activity at 50 to 70° C., and
   allowing the first bacteria and the second bacteria to be present in the organic waste,
   wherein the mesophilic bacterium is *Bacillus subtilis*.

2. The method of treating organic waste according to claim 1, which further comprises adding the mesophilic bacterium and the thermophilic bacterium to the organic waste.

3. The method of treating organic waste according to claim 1 or 2, which further comprises adding new organic waste to the organic waste in which the mesophilic bacterium and the thermophilic bacterium are present.

4. The method of treating organic waste according to claim 1, wherein the mesophilic bacterium or the thermophilic bacterium has a decomposition ability of organic matter.

5. The method of treating organic waste according to claim 1, wherein the mesophilic bacterium has an exothermic action.

6. The method of treating organic waste according to claim 1, wherein the mesophilic bacterium forms a spore at a temperature of 50° C. or higher.

7. The method of treating organic waste according to claim 1, wherein the mesophilic bacterium is a strain of *Bacillus subtilis* C-3102 (FERM BP-1096).

8. The method of treating organic waste according to claim 1, wherein the thermophilic bacterium belongs to the genus *Bacillus*.

9. The method of treating organic waste according to claim 8, wherein the thermophilic bacterium is *Bacillus pallidus*.

10. The method of treating organic waste according to claim 9, wherein the thermophilic bacterium is a strain of *Bacillus pallidus* TK6004 (FERM BP-0897).

11. The method of treating organic waste according to claim 1, wherein the mesophilic bacterium in said waste is present at a cell mass of from $1.0\times10^3$ to $1.0\times10^8$ CFU/g.

12. The method of treating organic waste according to claim 1, wherein the thermophilic bacterium in said waste is present at a cell mass of from $1.0\times10^3$ to $1.0\times10^8$ CFU/g.

13. The method of treating organic waste according to claim 1, wherein the organic waste is raw garbage, livestock waste, waste derived from sewage treatment, or industrial waste.

14. An agent for treating organic waste, comprising two different bacteria, wherein a first bacterium is a mesophilic bacterium which exerts its activity at 15 to 50° C. and a second bacterium is a thermophilic bacterium which exerts its activity at 50 to 70° C., wherein the mesophilic bacterium is *Bacillus subtilis*.

15. The agent for treating organic waste according to claim 14, wherein the mesophilic bacterium or the thermophilic bacterium has a decomposition ability of organic matter.

16. The agent for treating organic waste according to claim 14 or 15, wherein the mesophilic bacterium has an exothermic action.

17. The agent for treating organic waste according to claim 14, wherein the mesophilic bacterium forms a spore at a temperature of 50° C. or higher.

18. The agent for treating organic waste according to claim 14, wherein the mesophilic bacterium is a strain of *Bacillus subtilis* C-3102 (FERM BP-1096).

19. The agent for treating organic waste according to claim 14 or 15, wherein the thermophilic bacterium belongs to the genus *Bacillus*.

20. The agent for treating organic waste according to claim 19, wherein the thermophilic bacterium is *Bacillus pallidus*.

21. The agent for treating organic waste according to claim 20, wherein the thermophilic bacterium is a strain of *Bacillus pallidus* TK6004 (FERM BP-0897).

22. A method of treating organic waste, comprising treating the organic waste with two different bacteria, wherein a first bacterium is a mesophilic bacterium which exerts its activity at 15 to 50° C. and a second bacterium is a thermophilic bacterium which exerts its activity at 50 to 70° C., wherein the mesophilic bacterium and the thermophilic bacterium are present in the organic waste, and the mesophilic bacterium is *Bacillus subtilis*, and wherein an elevation of a temperature of the organic waste to a temperature at which the thermophilic bacterium exerts its activity is provided without an external apparatus and is due to the activity of the mesophilic bacterium at 15-50° C.

23. A method of treating organic waste, comprising treating the organic waste with two different bacteria, wherein a first bacterium is a mesophilic bacterium which exerts its activity at 15 to 50° C. and a second bacterium is a thermophilic bacterium which exerts its activity at 50 to 70° C., wherein the mesophilic bacterium and the thermophilic bacterium are added to the organic waste, and the mesophilic bacterium is *Bacillus subtilis*, and wherein an elevation of a temperature of the organic waste to a temperature at which the thermophilic bacterium exerts its activity is provided without an external apparatus and is due to the activity of the mesophilic bacterium at 15-50° C.

* * * * *